US00PP20680P2

(12) United States Plant Patent
Smith

(10) Patent No.: US PP20,680 P2
(45) Date of Patent: Jan. 26, 2010

(54) ***SALVIA* PLANT NAMED 'SHELL DANCER'**
(50) Latin Name: *Salvia hybrida*
Varietal Denomination: Shell Dancer

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/219,024

(22) Filed: Jul. 15, 2008

(51) Int. Cl.
*A01H 5/00* (2006.01)

(52) U.S. Cl. ..... Plt./475

(58) Field of Classification Search ..... Plt./263, Plt./475
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct *Salvia* plant is provided resulting from a controlled cross between an unnamed *Salvia microphylla* plant and a *Salvia×jamensis* 'Sierra San Antonio' plant. Seedlings were produced and the new cultivar resulted from the selective study of the resulting progeny. Multi-toned blossoms of good substance are prolifically formed over an extended period of time. The growth habit is bushy, and attractive large bright leaves are displayed. The plant also exhibits a propensity to vigorously regrow following pruning and is well suited to provide attractive ornamentation.

1 Drawing Sheet

Botanical/commercial classification: *Salvia hybrida/ Salvia* plant.

Varietal denomination: cv. Shell Dancer.

SUMMARY OF THE INVENTION

The new *Salvia* plant was created during 2004 at Watsonville, Calif., U.S.A., by artificial pollination wherein two parents were crossed which previously had been studied in the hope that they would contribute the desired characteristics. The female parent (i.e., the seed parent) of the new cultivar was an unnamed *Salvia microphylla* (non-patented in the United States). The male parent (i.e., the pollen parent was the *Salvia×jamensis* plant named 'Sierra San Antonio' (non-patented in the United States). The parentage of the new cultivar can be summarized as follows:

[*Salvia microphylla*]×[*Salvia×jamensis* 'Sierra San Antonio'].

The seeds resulting from the pollination were sown and small plants were obtained which were physically and biologically different from each other. Selective study resulted in the identification of a single plant of the new cultivar.

It was found that the new *Salvia* cultivar of the present invention displays the following combination of characteristics:

(a) displays a bushy growth habit,
(b) prolifically forms attractive substantial multi-toned blossoms over an extended period of time,
(c) displays attractive large bright leaves, and
(d) exhibits a propensity to vigorously regrow following pruning.

When compared to other known *Salvia* cultivars, the new cultivar of the present invention can be readily distinguished in view of the above combination of characteristics.

The new cultivar of the present invention can be grown to advantage to provide colorful ornamentation in gardens, in the landscapes, and in other residential settings.

The new cultivar can be readily distinguished from its ancestors. More specifically, the blossoms of the *Salvia microphylla* female parent are of a dissimilar solid pink coloration, and the blossoms of the male parent 'Sierra San Antonio' are a dissimilar yellow blushed with peach coloration. Also, the new cultivar can be readily distinguished from the 'Hot Lips' cultivar (non-patented in the United States) and the 'Wild Watermelon' cultivar (non-patented in the United States). More specifically, the blossoms of the 'Hot Lips' cultivar are a dissimilar cherry red and white coloration, and the blossoms of the 'Wild Watermelon' cultivar are a dissimilar solid hot pink coloration.

Asexual reproduction of the new cultivar by the rooting of cuttings has been carried out at Watsonville, Calif., U.S.A. Such propagation has confirmed that the unique combination of characteristics of the new cultivar has been stably established and is well transmitted to successive generations. The new cultivar asexually reproduces in a true-to-type manner.

It commonly takes approximately 14 days on average to initiate root development when the plant is asexually reproduced by the rooting of cuttings.

The new cultivar has been named 'Shell Dancer'.

BRIEF DESCRIPTION OF THE PHOTOGRAPHS

The accompanying photographs show as nearly true as it is reasonably possible to make the same in color illustrations of this character, typical specimens of the new cultivar. The plants were being grown under greenhouse production conditions near West Grove, Pa., U.S.A.

DETAILED BOTANICAL DESCRIPTION

Figure 1:
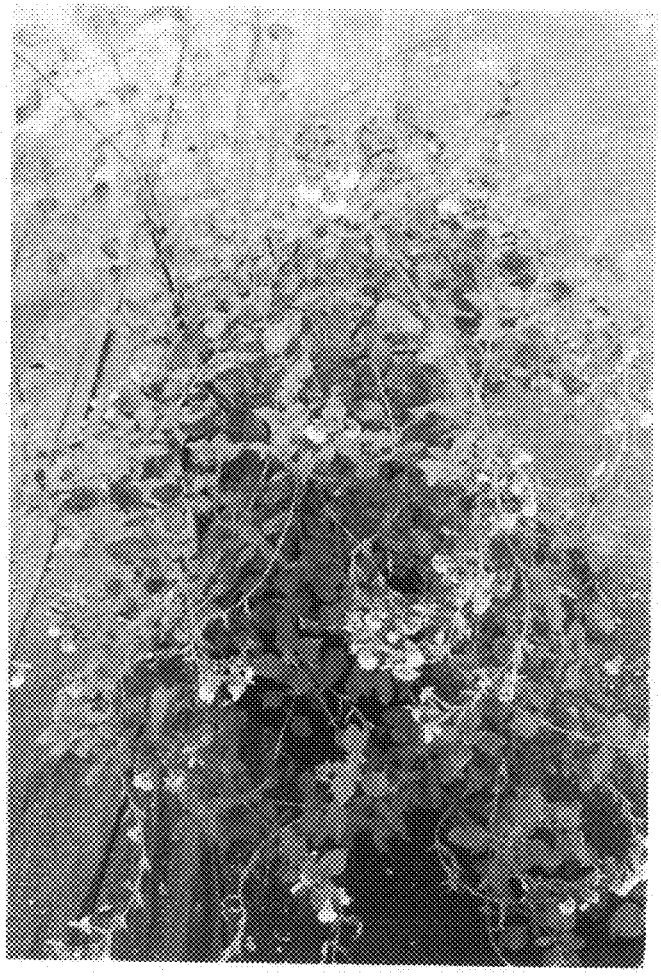
FIG. 1 shows an overall view of a typical flowering container-grown plant wherein the bushy growth habit and bright green foliage are apparent.
Figure 2:
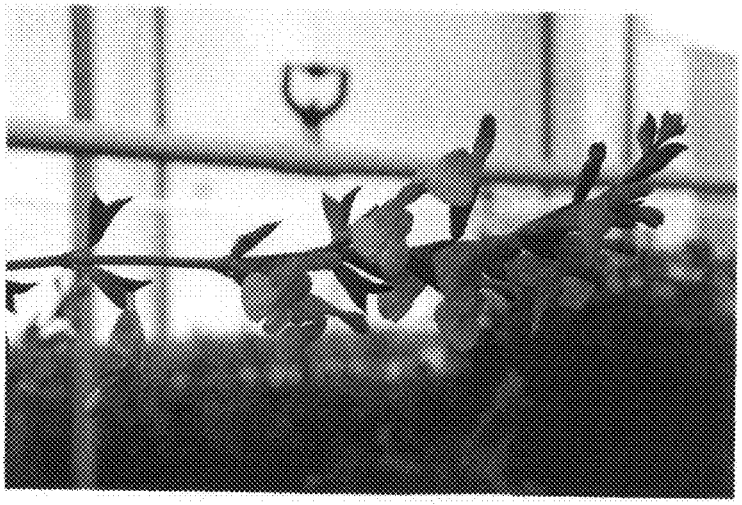
FIG. 2 shows a close view of the attractive multi-toned flowers of good substance.

The following is a detailed description of the new cultivar of the present invention which was prepared while observing one years-old plants growing in containers under greenhouse production conditions near West Grove, Pa., U.S.A. The plants had been asexually reproduced by the rooting of cuttings and were observed during May, 2008. Color terminology is in accordance with the R.H.S. Colour Chart of The Royal Horticultural Society, London, England, except when general color terms are used which are to be accorded their customary dictionary significance.

Type: Ornamental perennial shrub.

Plant:

*Growth habit.*—Bushy.

*Height.*—Commonly up to approximately 1 m on average.

*Width.*—Commonly up to approximately 1.3 m on average.

Foliage:

*Arrangement.*—Opposite.

*Shape.*—Elliptic to oblong.

*Size.*—Commonly approximately 3 to 3.5 cm in length on average and approximately 2 to 3 cm in width on average.

*Leaf thickness.*—Slightly fleshy.

*Margin.*—Crenate.

*Apex.*—Acute to obtusely rounded.

*Base.*—Substantially obtuse.

*Scent.*—When crushed the leaves exhibit a tangy and fruity scent.

*Color.*—Commonly near Green Group 137A on the upper surface, and near Green Group 138B on the under surface.

*Petioles.*—Somewhat flattened, commonly of variable lengths of approximately 5 to 9 mm, approximately 1 to 1.5 mm in width, and near Yellow-Green Group 145B in coloration.

Inflorescence:

*Time.*—Flowering commonly first occurs during May under greenhouse growing conditions near West Grove, Pa., U.S.A.

*Duration.*—Flowering commonly extends from May through November.

*Type.*—Terminal raceme.

*Length.*—Commonly approximately 20 cm on length.

*Number.*—Commonly approximately 70 to 80 flowers on average are borne on the plant at a given time during the flowering season.

*Shape.*—Tubular, and two-lipped.

*Pedicel length.*—Commonly approximately 3 to 4 mm.

*Pedicel width.*—Commonly approximately 2 mm..

*Pedicel texture.*—Glabrous.

*Pedicel color.*—Yellow-Green Group 145B.

*Calyx shape.*—Broadly campanulate, and flared towards the apex.

*Calyx ribs.*—Commonly approximately 10 in number and longitudinally arranged.

*Calyx length.*—Approximately 10 mm on average.

*Calyx width.*—Commonly up to approximately 5 mm on average.

*Calyx texture.*—Glandular and puberulent.

*Calyx color.*—Upper lobe: Yellow-Green Group 145B at the base and Violet Group 83D at the apex. lower lobes: primarily yellow-Green Group 145B.

*Calyx lobe number.*—1 upper lobe and 2 lower lobes.

*Calyx lobe shape.*—The upper and lower lobes are acute.

*Calyx lobe size.*—The upper lobe commonly is approximately 4 mm in length and width, and the lower lobe commonly is approximately 3 mm in length and approximately 4 mm in width.

*Corolla shape.*—Tubular proximally to two-lipped distally.

*Corolla length.*—Commonly approximately 2.2 to 2.5 cm on average.

*Corolla color.*—Near Yellow-White Group 158D at the base (not visible in the photographs), near Greyed-Purple Group 186B at the tube, and light pink/orange near Orange Group 26D at the lower lip.

*Corolla tube length.*—Commonly approximately 23 mm on average.

*Corolla tube width.*—Commonly approximately 3 mm on average.

*Corolla tube depth.*—Commonly approximately 7 mm.

*Corolla tube lip number.*—1 upper lip and 2 suborbicular lower lips.

*Corolla upper lip shape.*—Hood-like.

*Corolla upper lip length.*—Commonly approximately 9 mm on average.

*Corolla lower lip shape.*—Banner-like, extended downward, and obovate in configuration.

*Corolla lower lip length.*—Commonly approximately 12 mm on average.

*Corolla lower lip diameter.*—Commonly approximately 12 mm on average at the tip.

*Style length.*—Commonly approximately 2.5 cm on average.

*Style width.*—Commonly approximately 1 mm on average.

*Style attachment.*—To a four-lobed ovary between the lobes.

*Stamen number.*—2.

*Stamen shape.*—Like a seesaw.

*Filament length.*—Commonly approximately 6 mm on average.

*Connective length.*—Commonly approximately 12 mm on average.

*Anther attachment.*—At the outer end of the connective.

*Anther length.*—Approximately 2 mm on average.

I claim:

1. A new and distinct *Sylvia* plant having the following combination of characteristics:

(a) displays a bushy growth habit;

(b) prolifically forms attractive substantial multi-toned blossoms over an extended period of time;

(c) displays attractive large bright leaves, and (d) exhibits a propensity to vigorously regrow following pruning; substantially as illustrated and described.

* * * * *